United States Patent [19]

Bensmann

[11] Patent Number: 4,904,262
[45] Date of Patent: Feb. 27, 1990

[54] JOINT PROSTHESIS AND PROCESS FOR ITS MANUFACTURE

[75] Inventor: Günter Bensmann, Essen, Fed. Rep. of Germany

[73] Assignee: Fried. Krupp GmbH, Fed. Rep. of Germany

[21] Appl. No.: 191,642

[22] Filed: May 6, 1988

[30] Foreign Application Priority Data

May 6, 1987 [DE] Fed. Rep. of Germany ....... 3715000

[51] Int. Cl.[4] .............................................. A61F 2/30
[52] U.S. Cl. ...................................... 623/18; 623/901
[58] Field of Search ................... 623/16, 18, 20, 21, 623/22, 23

[56] References Cited

U.S. PATENT DOCUMENTS

| 4,287,617 | 9/1981 | Tornier | 623/23 |
| 4,595,393 | 6/1986 | Anapliotis et al. | 623/22 |
| 4,718,914 | 1/1988 | Frey et al. | 623/23 |

FOREIGN PATENT DOCUMENTS

| 2933237 | 3/1981 | Fed. Rep. of Germany | 623/18 |
| 2933271 | 3/1981 | Fed. Rep. of Germany | 623/18 |
| 3120147 | 12/1982 | Fed. Rep. of Germany | 623/23 |
| 2501998 | 9/1982 | France | 623/22 |

*Primary Examiner*—Richard J. Apley
*Assistant Examiner*—David J. Isabella
*Attorney, Agent, or Firm*—Sughrue, Mion, Zinn, Macpeak & Seas

[57] ABSTRACT

Joint prosthesis of perforated sheet metal strips which, for the formation of a hollow shaft, are welded together and to a collar having a protrusion for attaching to a ball joint. The collar is provided with an opening leading to the inside of the hollow shaft.

5 Claims, 2 Drawing Sheets

JOINT PROSTHESIS AND PROCESS FOR ITS MANUFACTURE

BACKGROUND OF THE INVENTION

The present invention relates to a joint prosthesis which is in the form of a shaft and which is constructed as a hollow body, and comprised of perforated sheet metal and having a collar and a projection onto which the joint is set.

In endoprosthesis there is currently a differentiation between two variations of attachment of the prosthesis shaft in the bone. The prostheses are either attached by means of a bone cement in the prepared bone cavity or by using so-called cementless prostheses.

As a rule, good initial success is obtained with the cementing technique, as the cement adapts very well to the prepared bone cavity. However, since the bone cement becomes brittle after a certain amount of time, the prostheses become loose and have to be removed.

It was attempted to counter this disadvantage with the development of the cementless prosthesis. In the cementless technique, prosthesis shafts having a surface structure are inserted into the bone cavity which has been prepared as precise as possible and are fixed there by means of pressure setting. In order to obtain a permanent fixation of the prosthesis, the bone has to grow into the surface structure. However, as the flexural strength of the protheses shaft is considerably higher than the flexural strength of the bone into which it has been implanted, relative movements occur on stress between the bone and the shaft, which leads to a connective tissue separation of the prosthesis shaft and thus a loosening.

A prosthesis is already known, as described in DE-OS No. 31 20 147, which has a shaft that is designed as a hollow body, comprised of perforated sheet metal and having a collar and a protrusion serving for the attachment of the ball joint. It is possible to introduce into the inside of the hollow prosthesis, after the primary fixation, cut up bone chips, which accrues in sufficient quantity during the operation. The hollow shaft of the prosthesis is provided with a sufficient number of various size holes so that the bone chips pressed into the shaft can come into contact with the wall of the bone cavity and grow onto it.

An essential difference to the current cementless prosthesis technology thus resides in the fact that the bone does not have to grow into the surface structure. It is much rather possible with this construction that, already during the operation, the bone is brought to the place where it is needed. By the adequate sizing of the holes in the prosthesis shaft it is possible to take care that the bone inserted into the shaft grows on and can be nourished permanently.

The design of the prosthesis shaft as a perforated hollow shaft also has the advantage that with the arrangement and sizing of the holes, the flexural strength of the shaft can largely be adjusted to the flexural strength of the bone, so that during stress of the system the bone/prosthesis relative motions are slight.

However, the perforated hollow prostheses such as described in DE-OS No. 31 20 147 cannot be manufactured with defensible technical expenditure.

SUMMARY OF THE INVENTION

It is an object of the present invention to provide a joint prosthesis which has the advantage of the known prosthesis, but can be manufactured simply and with defensible technical expenditure.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing object and in accordance with its purpose, the present invention provides a joint prothesis in the form of a shaft constructed as a hollow body, and comprised of perforated sheet metal and having a collar containing a protrusion for attaching a joint ball, wherein the shaft is comprised of individual, perforated strips of sheet metal which are welded together to form the hollow shaft, and the collar is welded at the upper end of the shaft, the collar having an opening leading to the inside of the hollow shaft, whereby it is possible to insert, after implantation of the protheses, through the collar opening ground or cup up bone chips.

The collar opening is used for filling the hollow shaft with bone clips, without removing the prosthesis head.

By constructing the prosthesis according to the present invention of individual strips of sheet metal, preshaped if needed, which are welded into a hollow shaft, the advantage can also be attained to get a flexural strength in the shaft which, on each place, approximately corresponds to the flexural strength of the bone for which it is designed. By a suitable arrangement and sizing of the holes, as well as by milling and grinding at suitable places, a reduced wall thickness of the sheet metal strips can be attained. The sheet metal strips, of which the hollow shaft is constructed, can have various thicknesses across their surface.

Preferably, CoCrMo, CoNiCrMo, titanium alloys, tantalum or niobium are used as the material of the metal strips, collar and protrusion.

In the process of the present invention for making the prosthesis, the diameter of the holes in the sheet metal pieces forming the hollow shaft preferably are sufficient so that the bone chips introduced into the hollow cavity can come into direct contact with the cancellous tissue of the bone. For obtaining the given flexural strength, the sheet metal strips preferably are provided with holes of certain sizes and at certain arrangements, before or after cutting, and/or the thickness of the sheet metal is reduced in certain areas by milling or grinding. The sheet metal strips are preshaped if needed. For forming the hollow shaft, the sheet metal strips are joined together by welding and connected by welding to the collar wich has a protrusion for attaching to a ball joint.

It is to be understood that both the foregoing general description and the following detailed description are exemplary and explanatory, but are not restrictive of the invention.

BRIEF DESCRIPTION OF THE DRAWINGS

The accompanying drawings, in which like numbers indicate like parts, illustrate examples of presently preferred embodiments of the invention and, together with the description, serve to explain the principles of the invention.

The drawings show an embodiment of the hollow prosthesis according to the invention as follows.

DETAILED DESCRIPTION OF THE INVENTION

Figure 1:
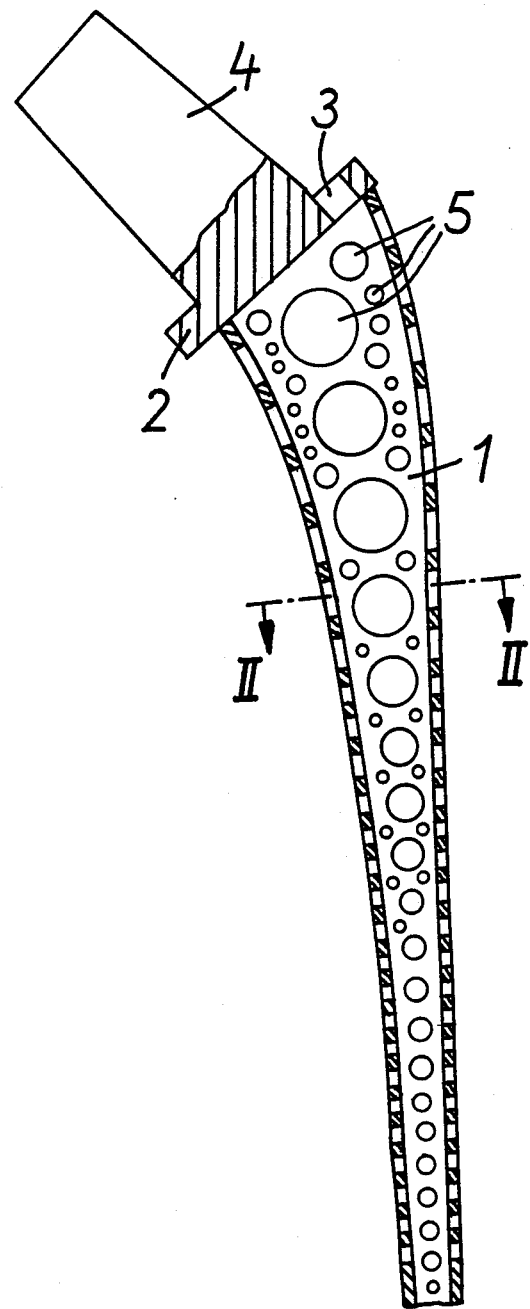
FIG. 1 is a longitudinal cut through a prosthesis made in accordance with the present invention.
Figure 2:
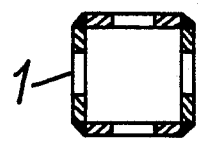
FIG. 2 is a cross-section taken along line II—II of FIG. 1.

Referring now to the drawings, the cross section of the prosthesis shown in FIG. 1 shows a collar 2 which is welded to a hollow shaft 1, the collar 2 having an opening 3 and a projection 4 for holding the ball joint. Hollow shaft 7 is comprised in this embodiment of four suitably cut and possibly preshaped pieces of sheet metal of CoCrMo which are welded together. The cross section of the hollow shaft is shown in FIG. 2. Through opening 3 in collar 2 the hollow shaft 1 can be filled with bone chips . The sheet metal pieces are provided with holes 5 of various arrangements and sizes in such a manner that the flexural strength of hollow shaft 1 agrees as closely as possible to the flexural strength of the bone. The calculation of the arrangement and distribution of holes 5 for a certain flexural strength can be determined, e.g., by the method of finite elements.

Figure 3:
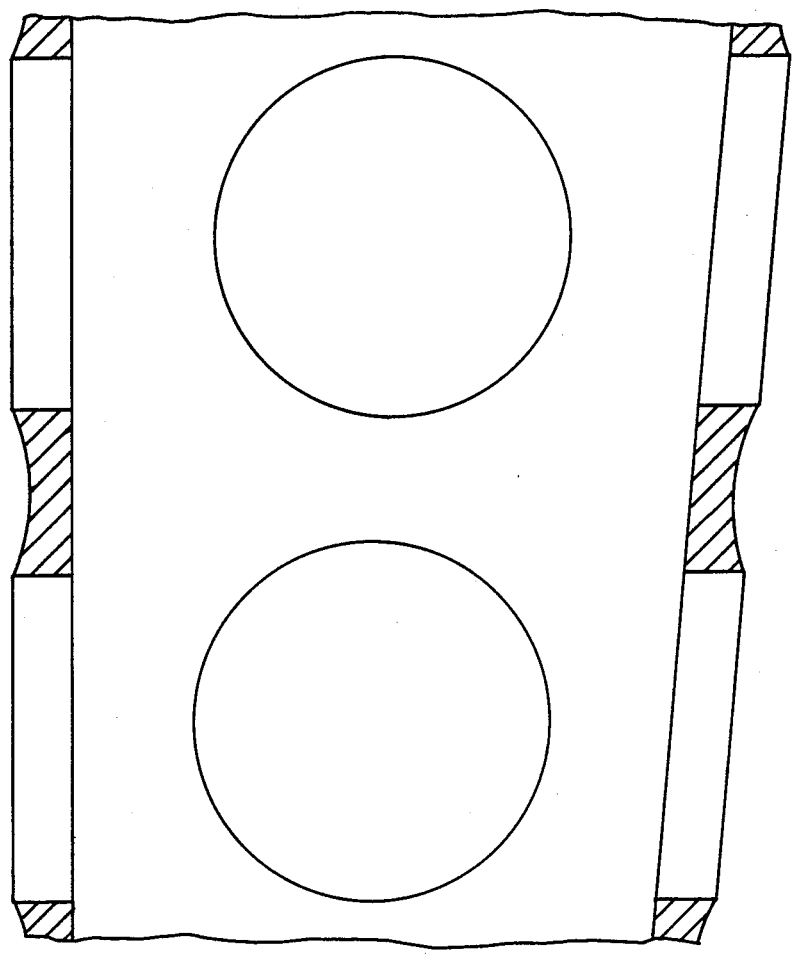
FIG. 3 is an enlarged longitudinal cut through a portion of the prosthesis of FIG. 1.

According to the further development of the prosthesis according to the invention, FIG. 3 shows in a section from the longitudinal cut, an example of a possible arrangement of the places of reduced sheet metal thickness by milling or grinding for fine adjustment of the flexural strength of the prosthesis.

It will be understood that the above description of the present invention is susceptible to various modifications, changes and adaptations, and the same are intended to be comprehended within the meaning and range of equivalents of the appended claims.

What is claimed is:

1. Joint prosthesis comprising (a) a hollow shaft comprised of a perforated sheet metal and (b) a collar attached to the shaft and containing a protrusion for attaching to a ball joint, wherein the shaft is comprised of individual, perforated strips of sheet metal which are welded together to form the hollow shaft, and the collar is welded at the upper end of the shaft, the collar having an opening leading to the inside of the hollow shaft, whereby it is possible to insert, after implantation of the prosthesis, through the collar opening ground or cut up bone chips .

2. Joint prosthesis according to claim 1, wherein the sheet metal strips, of which the hollow shaft is constructed, have a cross-section wall of varying thickness.

3. Joint prosthesis according to claim 1, wherein said sheet has a cross section containing areas of reduced thickness.

4. Joint prosthesis according to claim 1, wherein the material for the sheet metal and collar is selected from the group consisting of CoCrMo, CoNiCrMo, titanium alloys, tantalum and niobium.

5. Process for making a hollow prosthesis comprising (a) a hollow shaft comprised of a perforated sheet metal and (b) a collar attached to the shaft and containing a protrusion for attaching to a ball joint, wherein the shaft is comprised of individual, perforated strips of sheet metal which are welded together to form the hollow shaft, and the collar is welded at the upper end of the shaft, the collar having an opening leading to the inside of the hollow shaft, whereby it is possible to insert, after implantation of the prosthesis, through the collar opening ground or cut up bone chips, comprising welding the sheet metal strips together and welding the sheet metal strips to the collar which has a protrusion for attaching to a ball joint.

* * * * *